United States Patent [19]
Baba et al.

[11] Patent Number: 5,539,125
[45] Date of Patent: Jul. 23, 1996

[54] 1-AZABICYCLO[3.3.0]OCTAN DERIVATIVE, SALT THEREOF, PROCESS FOR THE PREPARATION OF SAME AND USE THEREOF AS HYPERMOTILITY AGENTS

[75] Inventors: Yutaka Baba; Toshinao Usui; Takuji Kakigami; Yoshiro Ozeki; Katsura Tsukamoto; Nobuyuki Itoh, all of Nagoya, Japan

[73] Assignee: Sanwa Kagaku Kenkyusho Co., Ltd., Nagoya, Japan

[21] Appl. No.: 489,709

[22] Filed: Jun. 13, 1995

[30] Foreign Application Priority Data

May 7, 1994 [JP] Japan ..................... 6-153440

[51] Int. Cl.$^6$ ............ C07D 403/12; C07D 405/12; C07D 487/04; A61K 31/40
[52] U.S. Cl. .................. 548/453; 548/454; 548/455
[58] Field of Search .................. 548/453, 454, 548/455; 514/413, 414, 415

[56] References Cited

FOREIGN PATENT DOCUMENTS

| | | |
|---|---|---|
| 60-169473 | 9/1985 | Japan . |
| 62-129279 | 6/1987 | Japan . |
| 62-234083 | 10/1987 | Japan . |
| 62-277376 | 12/1987 | Japan . |
| 1-104072 | 4/1989 | Japan . |
| 1-110684 | 4/1989 | Japan . |
| 1-501226 | 4/1989 | Japan . |
| 1-168686 | 7/1989 | Japan . |
| 2-289566 | 11/1990 | Japan . |
| 4-211685 | 8/1992 | Japan . |
| 4-295476 | 10/1992 | Japan . |

OTHER PUBLICATIONS

The Merck Index, 10th Ed. (1984) Entry No. 6063 p. 965.
"Novel Benzamides as Selective and Potent Gastrokinetic Agents. 2.$^1$ Synthesis and Structure–Activity Relationships of 4–Amino–5–chloro–2–ethoxy–N–[[4–(4–flurobenzyl)–2–morpholinyl]methyl]benzamide Citrate As–4370) and Related Compounds," Kato et al., J. Med. Chem., 1991, 34, pp. 616–624.
"5–Hydroxytryptamine$_4$ receptors mediate relaxation of the rat oesophageal tunica muscularis mucosae," G. S. Baxter et al., Naunyn–Schmiedeberg's Archives of Pharmacology, 1991, vol. 343 pp. 439–446.
Abstract of the 98th Annual Lecture Meeting in the Pharmacological, Society of Japan, p. 223, Apr. 3–5, 1978 (Engl. Trans 1.).

Primary Examiner—David B. Springer
Attorney, Agent, or Firm—Nikaido, Marmelstein, Murray & Oram

[57] ABSTRACT

There are disclosed a 1-azabicyclo[3.3.0]octan derivative of the formula

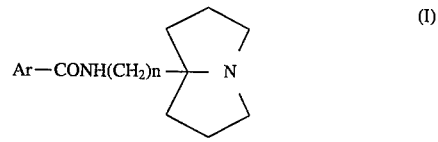

wherein n is an integer of 1–5; and Ar is an aromatic residue.
a pharmacologically acceptable salt of the compound, a process for the preparation of the compound and salt as well as use thereof as hypermotility agents.

6 Claims, No Drawings

1-AZABICYCLO[3.3.0]OCTAN DERIVATIVE, SALT THEREOF, PROCESS FOR THE PREPARATION OF SAME AND USE THEREOF AS HYPERMOTILITY AGENTS

BACKGROUND OF THE INVENTION

1. Field of the Invention

The present invention relates to a novel 1-azabicyclo [3.3.0]octan derivative, salt thereof, process for the preparation of same, and use thereof, for instance, a pharmaceutical composition for improving hypermotility of digestive tract, which contains the compound or salt as an effective ingredient.

2. Related Arts

Since 4-amino-5-chloro-N-[(2-diethylamino)ethyl]-2-methoxybenzamide [General name: Metoclopramide ("The Merck Index", 10th Ed. 6063)] had been developed in the 1960s, as an agent for improving hypermotility of digestive tract or anti-vomiting agent, various benzamide derivatives have been synthesized to evaluate pharmacological effect thereof. The main object for developing such derivatives lies in moderating a side effect of Metoclopramide to central nerve system due to its anti-dopamine action, namely extrapyramidal disorder and cryptorrhea (lactation and prolactinemia), and recent years, various reports have been issued on development of derivatives having antagonism to serotonin receptor.

A relation between a selective pharmacological activity and structure of these benzamide derivatives has not sufficiently been elucidated, but it has been recognized that a mutual relation between a substituent to amide nitrogen and alkoxy group at 2-position is important [for instance, Jap. Pat. Sho 62 (A.D. 1987) - 129279(A) and "J. Med. Chem.", Vol. 34, page 616 (1991)]. Under such a technical notion, carboxamide derivatives of benzofuran, benzopyran or indole have been studied, as compounds analogous to the benzamide derivatives [Jap. Pat. Sho 60 (A.D. 1985) - 169473(A), Sho 62 (A.D. 1987) - 234083(A), Hei 1 (A.D. 1989) - 104072(A), Hei 1 (A.D. 1989) - 110684(A), Hei 1 (A.D. 1989) - 168686(A), Hei 1 (A.D. 1989) - 501226(A), Hei 2 (A.D. 1990) - 289566(A). Hei 4 (A.D. 1992) - 211685(A), Hei 4 (A.D. 1992) - 298476(A), and WO 90/06113].

SUMMARY OF THE INVENTION

An object of the present invention is to provide a novel compound which has excellent or powerful action to activate $5\text{-}HT_4$ receptor and improve hypermotility of digestive tract and no or weak side effect to central nerve system, and thus is excellent in effectiveness and safety.

The inventors have energetically studied and investigated to finally find out that certain 1-azabicyclo[3.3.0]octan derivatives are suitable for attaining the object, so that the invention was established.

The 1-azabicyclo[3.3.0]octan derivatives according to the invention are shown by a formula of

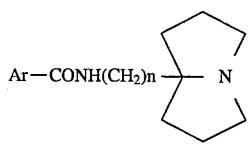

(I)

wherein n is an integer of 1–5; and Ar is an aromatic residue.

According to a process of the invention, the derivatives (I) and salts thereof can be prepared by reacting a compound of the formula

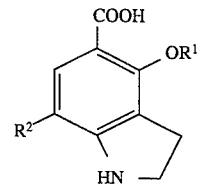

(II)

wherein $R^1$ is hydrogen atom or a lower alkyl group; and $R^2$ is hydrogen atom or halogen atom,

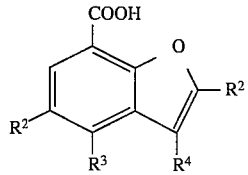

(III)

wherein $R^1$ and $R^2$ have the meanings as referred to; $R^3$ is an amino radical, a lower alkylamino group, or an acylamino group; and $R^4$ is a lower alkyl group, an unsaturated lower alkyl group or a lower alkenyl group, or

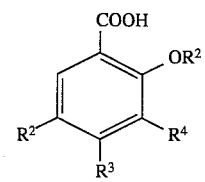

(IV)

wherein $R^1$, $R^2$, $R^3$ and $R^4$ have the meanings as referred to, or a reactive derivative thereof with a compound of the formula

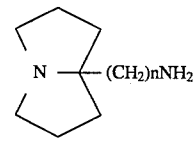

(V)

wherein n has the meaning as referred to.

and if necessary converting a reaction product into the salt.

In connection with the compounds (I), the lower alkyl group is such a straight- or branched-chain alkyl group having 1–6 carbon atoms as methyl, ethyl, propyl, isopropyl, butyl, heptyl and hexyl radicals. The unsaturated lower alkyl group is that having 1–6 carbon atoms, such as 2-propenyl and 2-butenyl radicals. The lower alkenyl is that having 1–6 carbon atoms, such as 1-propenyl and 1-butenyl radicals. As examples of the acylamino group, acetylamino and propionylamino radicals may be listed. The halogen atom may be of fluorine, chlorine, bromine or iodine.

The salt of the compounds (I) means, of course, pharmacologically acceptable one, and hydrochloric acid, sulfuric acid, hydrobromic acid or the like inorganic acid; and fumaric acid, oxalic acid, maleic acid, malic acid, tartaric acid, methanesulfonic acid or the like organic acid can be listed as that for forming the salt.

As the reactive derivative of compounds (II), (III) and (IV), a lower alkyl ester, active ester, acid anhydride, acid halide (especially acid chloride) or the like may be listed. As the active ester, p-nitrophenyl ester, 2,4,5-trichlorophenyl ester, pentachlorophenyl ester, cyanomethyl ester, N-hydroxysuccinic imide ester, N-hydroxy-5-norbornen-2,3-dicarboxyimide ester. N-hydroxypiperidine ester, 8-hydroxyquinoline ester, 2-hydroxyphenyl ester, 2-hydroxy-4,5-dichlorophenyl ester, 2-hydroxypyridine ester and 2-pyridylthiol ester can be exemplary listed. As the acid anhydride, a symmetrical acid anhydride or mixed acid anhydride can be employed. As the mixed acid anhydride, any mixture of ethyl chlorocarbonate, isobutyl chlorocarbonate, benzyl chlorocarbonate, phenyl chlorocarbonate and the like chlorocarbonic acid esters, or a mixture of the ester with an alkane acid such as isovaleic acid, pivalic acid or the like.

For the reaction between the compounds (II), (III) or (IV) and (V), a dehydration condensing agent may be added. Such an agent may be listed therefor as dicyclohexylcarbodiimide, hydrochloride of 1-ethyl-3-(3-dimethylaminopropyl)carbodiimide, N,N'-carbonyldiimidazole, 1-ethoxycarbonyl-2-ethoxy-1,2-dihydroquinoline or the like organic condensing agent; and phosphorous trichloride, phosphorous pentachloride, phosphorous oxychloride, thionyl chloride, silicon tetrachloride or the like inorganic condensing agent.

The reaction of the compound (II), (III), (IV) or its reactive derivative with the compound (V) can be carried out by stirring for 0.5–24 hours at −30°–+150° C. in an inert solvent. Such a solvent may be exemplary listed as benzene, toluene, xylene or the like aromatic hydrocarbon; diethylether, tetrahydrofuran, dioxane or the like ether; methylene chloride, chloroform or the like halogenated hydrocarbon: pyridine, quinoline, ethyl acetate, acetonitrile, dimethylformamide, dimethylsulfoxide, acetone, ethylene glycol, water, or a mixture of the above. If necessary, the reaction may be carried out in the presence of a base such as sodium carbonate, potassium carbonate or the like alkali carbonate: sodium hydrogen carbonate or the like alkali hydrogen carbonate; sodium hydroxide, potassium hydroxide or the like alkali hydroxide: triethylamine, N-methylmorpholine, N,N-dimethylaniline, pyridine, quinoline or the like tertiary amine. In lieu of separate addition of the base, the compound V may be used in an excess amount.

The starting compounds (III), (IV) and (V) can be synthesized in accordance with methods described, for instance, in WO 90/06133, Jap. Pat. Sho 62 (A.D. 1987) - 234083(A), Sho 62 (A.D. 1987) - 277376(A) and Hei 1 (A.D. 1989) - 110684(A). The other starting compound (II) can also be synthesized in accordance with a method described in "Abstract of the 98th Annual Lecture Meeting in the Pharmacological Society of Japan", page 223 (1978).

When a medicine shall be prepared by using the compound (I) or salt thereof as an effective ingredient, there is no limitation in form of the medicine and thus it can be made into a tablet, pill, capsule, powder, granule, suppository or the like solid preparation: or a solution, suspension, emulsion or the like liquid preparation. For preparing the solid preparation, a starch, lactose, glucose, calcium phosphate, magnesium stearate, carboxymethyl cellulose or the like filler can be used and if necessary, a lubricant, disintegrator, coating agent, coloring matter may also be used. The liquid preparation may contain a stabilizer, dissolution aid, suspending agent, emulsifier, buffer, preservative and the like.

An amount of dose of the compound (I) or salt thereof varies depending on a selected kind of the same, form of the medicine, symptom, age of a patient and other factors, but in general, such a range of about 0.01–about 50 mg/day is preferable for an adult.

DETAILED DESCRIPTION OF PREFERRED EMBODIMENTS

The invention will now be further explained in more detail with reference to Manufacturing Examples, Pharmacological Test Examples and Medicine Preparation Examples.

EXAMPLE 1

N-[2-(1-Azabicyclo[3.3.01]octan-5-yl)ethyl]-7-chloro-2, 3-dihydro-4-methoxyindole-5-carboxamide. ½ fumarate Into an agitating solution of 7-chloro-2,3-dihydro-4-methoxyindole- 5-carboxylic acid (100 mg) in absolute tetrahydrofuran (1 ml), was added 1,1-carbonylimidazole (72 mg) and after lapsed 1 hour, a solution of 5-(2-aminoethyl)-1-azabicyclo[3.3.0]octane (62 mg) was added therein to reflux for 1 hour. After cooled, the solvent was distilled out in vacuo, a residue was dissolved into chloroform, washed with saturated sodium carbonate solution and then water, and thereafter, the solvent was distilled out in vacuo. The resulting residue was refined by alumina column chromatography (developing solvent:chloroform) to afford 69 mg of N-[2-(1-azabicyclo[8.8.0]octan-5-yl)ethyl]- 7-chloro-2,3-dihydro-4-methoxyindol-5-carboxamide.

The compound was treated with fumaric acid in ethanol and lyophilized to quantitatively obtain the titled salt.

Mass spectrum (EI/DI) m/z:
363 (M⁺), 110.
NMR spectrum (DMSO-$d_6$) δ ppm:
| | |
|---|---|
| 1.63–1.89 | (10H, m), |
| 2.74 | (2H, m), |
| 3.16 | (2H, t), |
| 3.05–3.40 | (4H, m), |
| 3.16 | (1H, double d), |
| 3.58 | (2H, t), |
| 3.81 | (3H, s), |
| 6.14 | (1H, broad s), |
| 6.45 | (1H, s), |
| 7.48 | (1H, s), |
| 8.25 | (1H, broad t). |

EXAMPLE 2

N-[2-(1-Azabicyclo[3.3.0]octan-5-yl)ethyl]-7-chloro-2, 3-dihydro-4-ethoxyindole-5-carboxamide. ½ fumarate By treating as described in Example 1 excepting that 7-chloro-2,3-dihydro-4-ethoxyindole-5-carboxylic acid (100 mg) was selected as a starting compound, N-[2-(1-azabicyclo[3.3.0]octan-5-yl)ethyl]-7-chloro-2, 3-dihydro-4-ethoxyindole-5-carboxamide (143 mg) was obtained.

The compound was treated with fumaric acid in ethanol and lyophilized to quantitatively obtain the titled salt.

Mass spectrum (EI/DI) m/z:
377 (M⁺), 110.
NMR spectrum (DMSO-$d_6$) δ ppm:
| | |
|---|---|
| 1.29 | (3H, t), |
| 1.68–1.90 | (10H, m), |
| 2.70 | (2H, m), |
| 3.11 | (2H, t), |
| 3.15–3.40 | (4H, m), |
| 3.57 | (2H, t), |
| 4.05 | (2H, q), |
| 6.13 | (1H, s), |
| 6.45 | (1H, s), |
| 7.45 | (1H, s), |
| 8.12 | (1H, broad t). |

EXAMPLE 3

4-Amino-N-[2-(1-Azabicyclo[3.3.0]octan-5-yl)ethyl]-3-chloro-2-methylbenzo[b]furan-7-carboxamide.½ fumarate By treating as described in Example 1 excepting that 4-amino-3-chloro-2-methylbenzo[b]furan-7-carboxylic acid (60 mg) was selected as a starting compound, 4-amino-N-[2-(1-azabicyclo[3.3.0]octan-5-yl)ethyl]-3-chloro-2-methylbenzo[b]furan-7-carboxamide (96 mg) was obtained.

The compound was treated with fumaric acid in ethanol to quantitatively obtain the titled salt.

Melting point: 252–256° C.
Mass spectrum (EI/DI) m/z:
361 (M+), 110.
NMR spectrum (DMSO-d$_6$) δ ppm:

| | |
|---|---|
| 1.69–1.88 | (10H, m), |
| 2.42 | (3H, s), |
| 2.72 | (2H, m), |
| 3.13 | (2H, m), |
| 3.45 | (2H, m), |
| 5.88 | (2H, broad s), |
| 6.47 | (1H, s), |
| 6.48 | (1H, d), |
| 7.52 | (1H, s), |
| 8.15 | (1H, broad t). |

EXAMPLE 4

4-Amino-N-[2-(1-azabicyclo[3.3.0]octan-5-yl)ethyl]-5-chloro-2-methylbenzo[b]furan-7-carboxamide. ½ fumarate By treating as described in Example 1 excepting that 4-amino- 5-chloro-2-methylbenzo[b]furan-7-carboxylic acid (100 mg) was selected as a starting compound, 4-amino-N-[2-(1-azabicyclo[3.3.0]octan-5-yl)ethyl]-5-chloro-2-methylbenzo[b]furan-7-carboxamide (146 mg) was obtained.

The compound was treated with fumaric acid in ethanol to quantitatively obtain the titled salt.

Melting point: 242–253° C.
Mass spectrum (EI/DI) m/z:
361 (M+), 110.
NMR spectrum (DMSO-d$_6$) δ ppm:

| | |
|---|---|
| 1.60–1.90 | (10H, m), |
| 2.45 | (3H, m), |
| 2.73 | (2H, m), |
| 3.08 | (2H, m), |
| 3.41 | (2H, m), |
| 5.88 | (2H, broad s), |
| 6.47 | (1H, s), |
| 7.62 | (1H, s), |
| 8.35 | (1H, broad s). |

EXAMPLE 5

4-Amino-N-[2-(1-azabicyclo[3.3.0]octan-5yl)ethyl]-3,5-dichloro-2-methylbenzo[b]furan-7-carboxamide. ½ fumarate By treating as described in Example 1 excepting that 4-amino-3,5-dichloro-2-methylbenzo[b]furan-7-carboxylic acid (100 mg) was selected as a starting compound, 4-amino-N-[2-(1-azabicyclo[3.3.0]octan-5-yl)ethyl]-3,5-dichloro-2-methylbenzo[b]furan-7-carboxamide (150 mg) was obtained.

The compound was treated with fumaric acid in ethanol to quantitatively obtain the titled salt.

Melting point: 228–236° C.
Mass spectrum (EI/DI) m/z:
396 (M+), 110.
NMR spectrum (CDCl$_3$) δ ppm:

| | |
|---|---|
| 1.52 | (3H, d), |
| 1.52–1.83 | (10H, m), |
| 2.55–2.68 | (3H, m), |
| 2.97–3.06 | (2H, m), |
| 3.16 | (1H, double d), |
| 3.45–3.53 | (2H, m), |
| 4.18 | (2H, broad), |
| 5.07–5.15 | (1H, m), |
| 8.79 | (1H, s), |
| 7.99 | (1H, broad). |

EXAMPLE 6

4-Amino-N-[2-(1-azabicyclo[3.3.0]octan-5-yl)ethyl]-5-chloro-2-methoxy-3-propylbenzamide. ½ fumarate By treating as described in Example 1 excepting that 4-amino- 5-chloro-2-methoxy-3-propylbenzoic acid (100 mg) was selected as a starting compound, 4-amino-N-[2-(1-azabicyclo[3.3.0]octan-5-yl)ethyl]-5-chloro-2-methoxy-3-propylbenzamide (143 mg) was obtained.

The compound was treated with fumaric acid in ethanol and lyophilized to quantitatively obtain the titled salt.

Mass spectrum (EI/DI) m/z:
379 (M+), 110.
NMR spectrum (DMSO-d$_6$) δ ppm:

| | |
|---|---|
| 0.84 | (3H, t), |
| 1.42–1.85 | (12H, m), |
| 2.50 | (2H, m), |
| 2.72 | (2H, m), |
| 3.09 | (2H, double center), |
| 3.30 | (2H, m), |
| 3.63 | (3H, s), |
| 5.49 | (2H, broad s), |
| 6.45 | (1H, s), |
| 7.43 | (1H, s), |
| 8.30 | (1H, broad t). |

EXAMPLE 7

4-Amino-N-[2-(1-azabicyclo[3.3.0]octan-5-yl)ethyl]-5-chloro- 2-ethoxy-3-propylbenzamide. ½ fumarate By treating as described in Example 1 excepting that 4-amino- 5-chloro-2-ethoxy-8-propylbenzoic acid (100 mg) was selected as a starting compound, 4-amino-N-[2-(1-azabicyclo[3.3.0]octan-5-yl)ethyl]-5-chloro-2-ethoxy-8-propylbenzamide (97 mg) was obtained.

The compound was treated with fumaric acid in ethanol and lyophilized to quantitatively obtain the titled salt.

Mass spectrum (EI/DI) m/z:
393 (M+), 110.
NMR spectrum (DMSO-d$_6$) δ ppm:

| | |
|---|---|
| 0.95 | (3H, t), |
| 1.32 | (3H, t), |
| 1.40–1.84 | (12H, m). |
| 2.51 | (2H, m), |
| 2.68 | (2H, m), |
| 3.10 | (2H, broad center), |
| 3.30 | (2H, m), |
| 5.47 | (2H, broad s), |
| 6.44 | (1H, s), |
| 7.39 | (1H, s), |
| 8.18 | (1H, s). |

REFERENCE EXAMPLE 1

4-Amino-5-chloro-2-methoxy-3-(2-propenyl)benzoic acid

A mixture of methyl ester of 4-acetylamino-5-chloro-2-methoxy- 3-(2-propenyl)benzoic acid (460 mg), 4N-sodium hydroxide (4 ml) and methanol (4 ml) was refluxed for 16 hours. After cooled, the reaction mixture was neutralized under ice-cooling to obtain formed crystals (360 mg) which are desired compound.

The product contains a structural isomer (about 20% by weight) of 4-amino-5-chloro-2-methoxy-3-(1-propenyl)benzoic acid.

| NMR spectrum (CDCl$_3$) δ ppm: | |
|---|---|
| 3.45 | (2H, double d), |
| 3.87 | (3H, s), |
| 4.68 | (2H, broad s), |
| 5.01–5.15 | (2H, m), |
| 5.91–6.01 | (1H, m), |
| 8.02 | (2H, m). |
| Structural isomer | |
| NMR spectrum (CDCl$_3$) δ ppm: | |
| 2.01 | (3H, d), |
| 3.85 | (3H, s), |
| 4.79 | (2H, broad s), |
| 6.21 | (1H, double d), |
| 6.23 | (1H, d), |
| 7.97 | (1H, s). |

EXAMPLE 8

4-Amino-N-[2-(1-azabicyclo[3.3.0]octan-5-yl)ethyl]-5-chloro-2-methoxy-3-(2-propenyl)benzamide. ½ fumarate By treating as described in Example 1 excepting that 4-amino- 5-chloro-2-methoxy-3-(2-propenyl)benzoic acid (100 mg) obtained by Reference Example 1 was selected as a starting compound. 4-amino-N-[2-(1-azabicyclo[3.3.0]octan-5-yl)ethyl]-5-chloro- 2-methoxy-3-(2-propenyl)benzamide (130 mg) was obtained. The product contains a structural isomer (about 20% by weight) of 4-amino-N-[2-(1-azabicyclo[3.3.0]octan-5-yl)ethyl]-5-chloro-2-methoxy-3-(1-propenyl)benzamide.

The compound was treated with fumaric acid in ethanol and lyophilized to quantitatively obtain the titled salt.

| Mass spectrum (EI/DI) m/z: | |
|---|---|
| 377 (M$^+$), 110. | |
| NMR spectrum (DMSO-d$_6$) δ ppm: | |
| 1.51–1.92 | (10H, m), |
| 2.72 | (2H, m), |
| 3.01–3.40 | (8H, m), |
| 3.64 | (3H, s), |
| 5.04 | (2H, double q), |
| 5.44 | (2H, broad s), |
| 5.81–5.95 | (1H, s), |
| 6.45 | (1H, s), |
| 7.51 | (1H, s), |
| 8.29 | (1H, broad t). |

REFERENCE EXAMPLE 2

4-Amino-5-chloro-2-ethoxy-3-(2-propenyl)benzoic acid

A mixture of methyl ester of 4-acetylamino-5-chloro-2-ethoxy-3-(2-propenyl)benzoic acid (660 mg), 4N-sodium hydroxide (4 ml) and methanol (6 ml) was refluxed for 24 hours. After cooled, the reaction mixture was neutralized under ice-cooling to obtain formed crystals (380 mg) which are desired compound.

The product contains a structural isomer (about 25% by weight) of 4-amino-5-chloro-2-ethoxy-3-(1-propenyl)benzoic acid.

| NMR spectrum (CDCl$_3$) δ ppm: | |
|---|---|
| 1.40 | (3H, t), |
| 3.44 | (2H, double t), |
| 4.05 | (2H, q), |
| 4.77 | (2H, broad s), |
| 5.15 | (2H, m), |
| 5.95 | (1H, m), |
| 7.87 | (1H, s). |
| Structural isomer | |
| NMR spectrum (CDCl$_3$) δ ppm: | |
| 1.40, 1.88 | (3H, each t), |
| 1.64, 1.99 | (3H, each d), |
| 4.03, 4.05 | (2H, each q), |
| 4.60, 4.67 | (2H, each s), |
| 6.05–6.30 | (2H, m), |
| 8.02, 8.03 | (1H, each s). |

EXAMPLE 9

4-amino-N-[2-(1-azabicyclo[3.3.0]octan-5-yl)ethyl]-5-chloro-2-ethoxy-3-(2-propenyl)benzamide. ½ fumarate By treating as described in Example 1 excepting that 4-amino-5-chloro-2-ethoxy-3-(2-propenyl)benzoic acid (100 mg) obtained by Reference Example 2 was selected as a starting compound, 4-amino-N-[2-(1-azabicyclo[3.3.0]octan-5-yl)ethyl]-5-chloro-2-ethoxy-3-(2-propenyl)benzamide (136 mg) was obtained. The product contains a structural isomer (about 25% by weight) of 4-amino-N-[2-(1-azabicyclo[3.3.0]octan-5-yl)ethyl]-5-chloro-2-ethoxy- 3-(1-propenyl)benzamide.

The compound was treated with fumaric acid in ethanol and lyophilized to quantitatively obtain the titled salt.

| Mass spectrum (EI/DI) m/z: | |
|---|---|
| 391 (M$^+$), 110. | |
| NMR spectrum (DMSO-d$_6$) δ ppm: | |
| 1.25 | (3H, t), |
| 1.55–1.93 | (10H, m), |
| 2.71 | (2H, m), |
| 3.00–3.60 | (8H, m), |
| 3.79 | (2H, q), |
| 5.00 | (2H, m), |
| 5.46 | (2H, broad s), |
| 5.80–6.02 | (1H, m), |
| 6.44 | (1H, s), |
| 7.48 | (1H, s), |
| 8.29 | (1H, broad t). |

PHARMACOLOGICAL TEST EXAMPLE 1

(Agonisting Action to 5-HT$_4$ Receptor)

Each of the compounds obtained by Examples and Cisapride (exemplar known compound which has been said as having a strong agonisting action to 5-HT$_4$ receptor) were selected as Test Compounds and Control compound, and agonisting action thereof was checked in accordance with the method described by Baxter et al. ["Naunyn-Schmiederberg's Arch. Pharmacol.", Vol. 343, page 439 (1991)].

Namely, a relaxation of the Test and Control compounds in various concentration showing to carbachol contradiction of a muscular sample of mucous membrane in esophgus exentrated from a rat was checked to calculate a concentration causing 50% relaxation and compared with its negative logarithm ($_p$EC$_{50}$). Results are shown in following Table 1. Therefrom, it has been found that the compounds according to the invention show the agonisting action to 5-HT$_4$ receptor, which is compatible to or excellent than the Control Compound.

TABLE 1

| Compound | pEC$_{50}$ |
|---|---|
| Example | |
| 1 | 5.3 |
| 2 | 5.3 |
| 3 | 5.7 |
| 4 | 7.4 |
| 5 | 6.1 |
| 6 | 6.3 |
| 7 | 6.4 |
| 8 | 6.3 |
| 9 | 6.3 |
| Cisapride | 7.4 |

PHARMACOLOGICAL TEST EXAMPLE 2

(Anti-dopamine Action)

The compounds (salts) obtained by Examples as well as known compound (Metoclopramide) were selected as Test and Control Compounds, respectively. The compound was orally administered to rats to observe for 2 days general symptoms including catalepsy and blepharoptosis due to antagonistic action of the compound to dopamine $D_2$ receptor.

In each case of the compounds according to the invention, no influence to central nerve system due to anti-dopamine action can be recognized in single administration of 500 mg/kg, but in case of Metoclopramide, somewhat remarkable influence was recognized in single administration of 100 mg/kg.

MEDICINE PREPARATION EXAMPLE 1
(TABLET)

Tablets were prepared in conventional manner and by using following ingredients.

| Fumarate (Example 4) | 2.0 (mg) |
|---|---|
| Lactose | 136.0 |
| Corn starch | 60.0 |
| Magnesium stearate | 2.0 |
| | 200.0 mg/tablet |

MEDICINE PREPARATION EXAMPLE 2
(INJECTION)

An injection was prepared in conventional manner and by using following ingredients. The injection was charged into ampules under aseptic condition to heat seal the ampules. When it shall be used, the solution in the ampule will be diluted with a saline for injection.

| Fumarate (Example 7) | 0.05 (mg) |
|---|---|
| Sodium chloride | 8.00 |
| Distilled water for injection | Remainder |
| | 1.0 ml/ampule |

What is claimed is:
1. A 1-azabicyclo [3.3.0]octan derivative of the formula

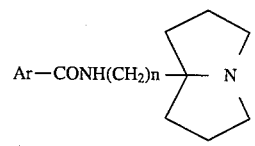

wherein n is an integer of 1–5; and Ar is selected from the group consisting of

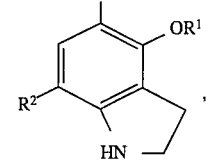

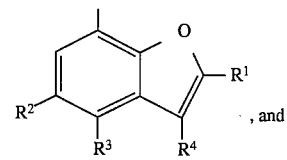

, and

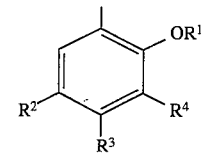

in which $R^1$ is hydrogen atom or a lower alkyl group; $R^2$ is hydrogen atom or halogen atom; $R^3$ is an amino radical, a lower alkylamino group or an acylamino group; and $R^4$ is a lower alkyl group, 2-propenyl radical, 2-butenyl radical, 1-propenyl radical or 1-butenyl radical, or a pharmacologically acceptable salt thereof.

2. The 1-azabicyclo[3.3.0]octan derivative as claimed in claim 1, wherein said compound is selected from the group consisting of (a) N-[2-(1-azabicyclo[3.3.0]octan-5-yl)ethyl]-7-chloro-2,3-dihydro-4-methoxyindole-5-carboxamide, (b) N-[2-(1-azabicyclo[3.3.0]octan-5-yl)ethyl]-7-chloro-2,3-dihydro-4-ethoxyindole-5-carboxamide, (c) 4-amino-N-[2-(1-azabicyclo[3.3.0]octan-5-yl)ethyl]-3-chloro-2-methylbenzo[b]furan-7-carboxamide, (d) 4-amino-N-[2-(1-azabicyclo[3.3.0]octan-5-yl)ethyl]-5-chloro-2-methylbenzo[b]furan-7-carboxamide, (e) 4-amino-N-[2-(1-azabicyclo[3.3.0]octan-5-yl)ethyl]-3,5-dichloro-2-methylbenzo[b]furan-7-carboxamide, (f) 4-amino-N-[2-(1-azabicyclo[3.3.0]octan-5-yl)ethyl]-5chloro-2-methoxy-3-propylbenzamide, (g) 4-amino-N-[2-(1-azabicyclo[3.3.0]octan-5-yl)ethyl]-5-chloro-2-ethoxy-3-propylbenzamide, (h) 4-amino-N-[2-(1-azabicyclo[3.3.0]octan-5-yl)ethyl]-5-chloro-2-methoxy-3-(1-propenyl)benzamide, (i) 4-amino-N-[2-(1-azabicyclo[3.3.0]octan-5-yl)ethyl]-5-chloro- 2-methoxy-3-(2-propenyl)benzamide, (j) 4-amino-N-[2-(1-azabicyclo[3.3.0]octan-5-yl)ethyl]-5-chloro-2-ethoxy-3-(1-propenyl)benzamide, and (k) 4-amino-N-[2-(1-azabicyclo[3.3.0]octan-5-yl)ethyl]-5-chloro-2-ethoxy-3-(2-propenyl)benzamide.

3. A process for the preparation of 1-azabicyclo[3.3.0] octan derivative of the formula

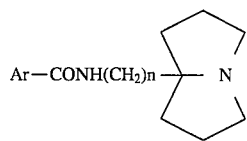

(I)

wherein n is an integer of 1–5; and Ar is selected from the group consisting of

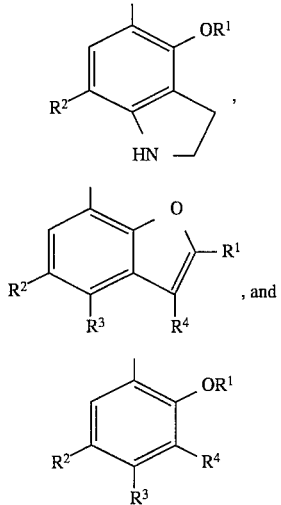

in which $R^1$ is hydrogen atom or a lower alkyl group; $R^2$ is hydrogen atom or halogen atom; $R^3$ is an amino radical, a lower alkylamino group or an acylamino group; and $R^4$ is a lower alkyl group, 2-propenyl radical, 2-butenyl radical, 1-propenyl radical or 1-butenyl radical, or a pharmacologically acceptable salt thereof, comprising stirring for 0.5–24 hours at −30°–+150° C. in an inert solvent a compound of the formula

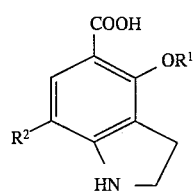

(II)

wherein $R^1$ is hydrogen atom or a lower alkyl group; and $R^2$ is hydrogen atom or halogen atom,

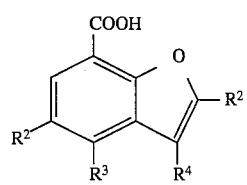

(III)

wherein $R^1$ and $R^2$ have the meanings as referred to; $R^3$ is an amino radical, a lower alkylamino group or an acylamino group; and $R^4$ is a lower alkyl group, 2-propenyl radical, 2-butenyl radical, 1-propenyl radical or 1-butenyl radical, or

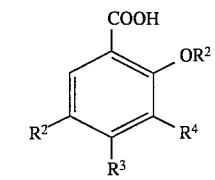

(IV)

wherein $R^1$, $R^2$, $R^3$ and $R^4$ have the meanings as referred to, or a reactive derivative thereof with a compound of the formula

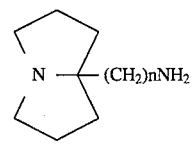

(V)

wherein n has the meaning as referred to, and if necessary, converting a reaction product into the salt.

4. A pharmaceutical composition suitable for improving hypermotility of a digestive tract, comprising an effective amount of a 1-azabicyclo[3.3.0]octan derivative of the formula

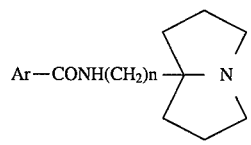

(I)

wherein n is an integer of 1–5; and Ar is selected from the group consisting of

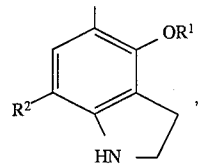

(VI)

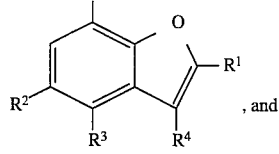

(VII)

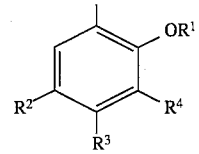

(VIII)

in which $R^1$ is hydrogen atom or a lower alkyl group; $R^2$ is hydrogen atom or halogen atom; $R^3$ is an amino radical, a lower alkylamino group or an acylamino group, and $R^4$ is a lower alkyl group, 2-propenyl radical, 2-butenyl radical, 1-propenyl radical or 1-butenyl radical, or a pharmacologically acceptable salt of the compound, in association with a pharmaceutically acceptable carrier or excipient.

5. The pharmaceutical composition as claimed in claim 4, wherein said 1-azabicyclo[3.3.0]octan derivative is selected from the group consisting of (a) N-[2-(1-azabicyclo[3.3.0]octan-5-yl)ethyl]-7-chloro-2,3-dihydro-4-methoxyindole-5-carboxamide,
(b) N-[2-(1-azabicyclo[3.3.0]octan-5-yl)ethyl]-7-chloro-2,3-dihydro-4-ethoxyindole-5-carboxamide,
(c) 4-amino-N-[2-(1-azabicyclo[3.3.0]octan-5-yl)ethyl]-3-chloro-2-methylbenzo[b]furan-7-carboxamide,
(d) 4-amino-N-[2-(1-azabicyclo[3.3.0]octan-5-yl)ethyl]-5-chloro-2-methylbenzo[b]furan-7-carboxamide,
(e) 4-amino-N-[2-(1-azabicyclo[3.3.0]octan-5-yl)ethyl]-3,5-dichloro-2-methylbenzo[b]furan-7-carboxamide,
(f) 4-amino-N-[2-(1-azabicyclo[3.3.0]octan-5-yl)ethyl]-5-chloro-2-methoxy-3-propylbenzamide,
(g) 4-amino-N-[2-(1-azabicyclo[3.3.0]octan-5-yl)ethyl]-5-chloro-2-ethoxy-3-propylbenzamide,
(h) 4-amino-N-[2-(1-azabicyclo[3.3.0]octan-5-yl)ethyl]-5-chloro-2-methoxy-3-(1-propenyl)benzamide,
(i) 4-amino-N-[2-(1-azabicyclo[3.3.0]octan-5-yl)ethyl]-5-chloro-2-methoxy-3-(2-propenyl)benzamide,
(j) 4-amino-N-[2-(1-azabicyclo[3.3.0]octan-5-yl)ethyl]-5-chloro-2-ethoxy-3-(1-propenyl)benzamide, and
(k) 4-amino-N-[2-(1-azabicyclo[3.3.0]octan-5-yl)ethyl]-5-chloro-2-ethoxy-3-(2-propenyl)benzamide.

6. A method for improving hypermotility of a digestive tract, comprising administering to a patient in need of such treatment an effective amount of the formula

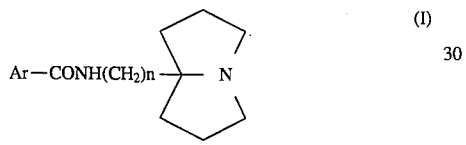
(I)

wherein n is an integer of 1–5; and Ar is selected from the group consisting of

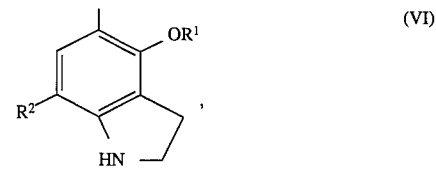
(VI)

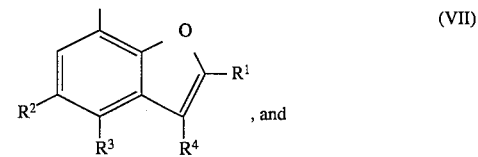
, and
(VII)

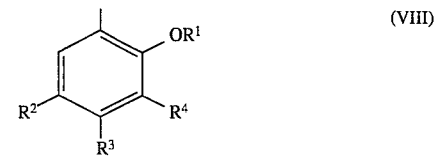
(VIII)

in which $R^1$ is hydrogen atom or a lower alkyl group: $R^2$ is hydrogen atom or halogen atom; $R^3$ is an amino radical, a lower alkylamino group or an acylamino group; and $R^4$ is a lower alkyl group, 2-propenyl radical, 2-butenyl radical, 1-propenyl radical or 1-butenyl radical, or a pharmacologically acceptable salt of the compound, in association with a pharmaceutically acceptable carrier or excipient.

* * * * *